Figures 1, 2:
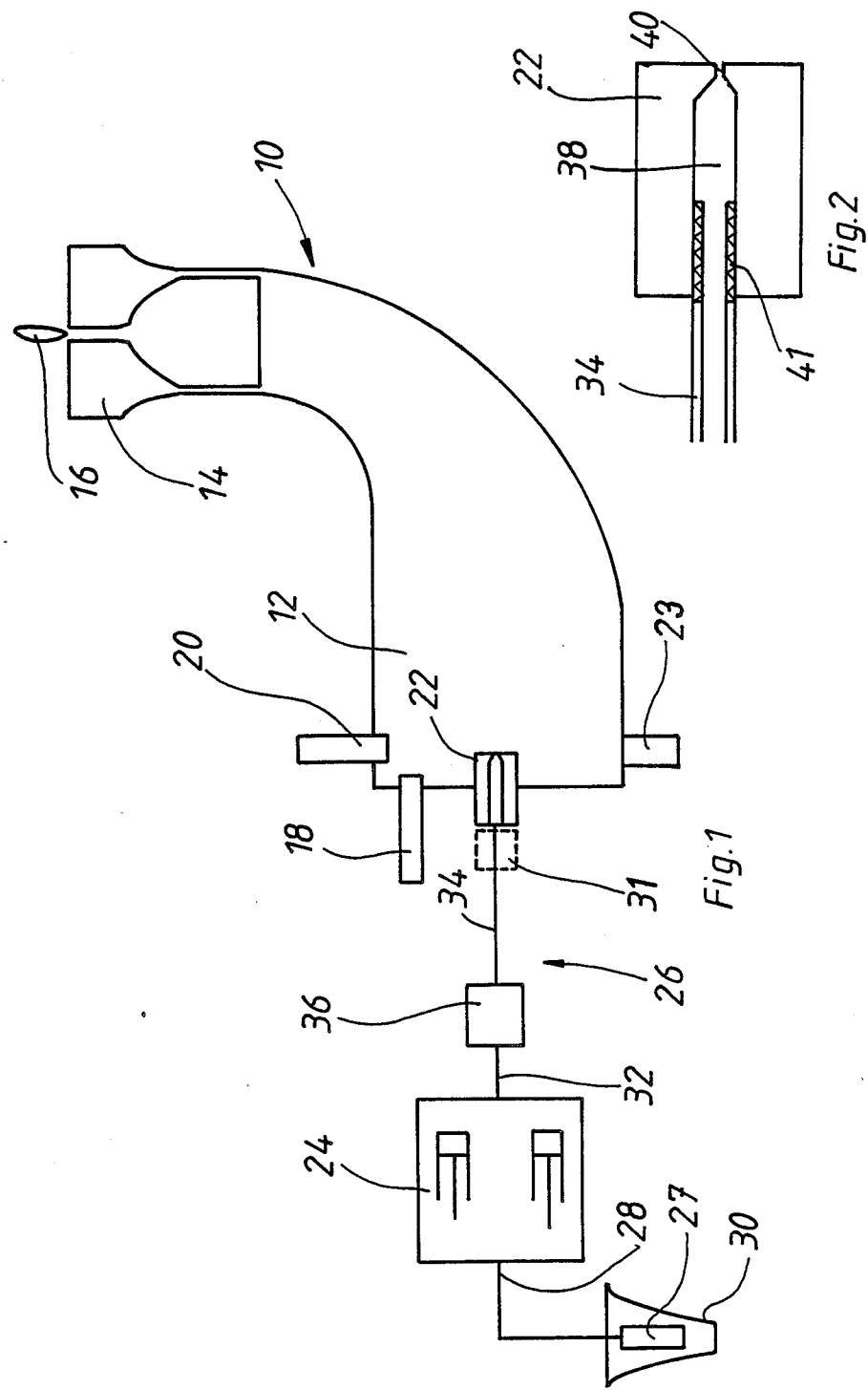

United States Patent [19]

Berndt

[11] Patent Number: 4,886,359

[45] Date of Patent: Dec. 12, 1989

[54] DEVICE FOR NEBULIZING SAMPLE LIQUID FOR SPECTROSCOPICAL PURPOSES

[76] Inventor: Harald Berndt, Auf der Bokkenbredde 48, 4600 Dortmund 41, Fed. Rep. of Germany

[21] Appl. No.: 256,238

[22] Filed: Oct. 11, 1988

Related U.S. Application Data

[63] Continuation of Ser. No. 872,885, Jun. 11, 1986, abandoned.

[30] Foreign Application Priority Data

Jun. 15, 1985 [DE] Fed. Rep. of Germany ....... 3521529

[51] Int. Cl.⁴ ................... G01N 21/72; G01N 21/73; G01N 21/74
[52] U.S. Cl. .................................. 356/312; 356/315; 356/316
[58] Field of Search ............... 356/312, 316, 315, 417

[56] References Cited

U.S. PATENT DOCUMENTS

| | | | |
|---|---|---|---|
| 4,306,175 | 12/1981 | Schleicher et al. | 356/316 X |
| 4,361,401 | 11/1982 | Smith, Jr. et al. | 356/312 |
| 4,517,495 | 5/1985 | Piepmeier | 356/316 X |
| 4,575,609 | 3/1986 | Fassel et al. | 356/316 |

FOREIGN PATENT DOCUMENTS

| | | |
|---|---|---|
| 0152891 | 8/1985 | European Pat. Off. ............ 239/589 |
| 2144642 | 3/1972 | Fed. Rep. of Germany . |
| 3026155 | 2/1982 | Fed. Rep. of Germany . |
| 3233130 | 3/1984 | Fed. Rep. of Germany ...... 356/315 |

OTHER PUBLICATIONS

Schrenk, W. G., "Historical Development of Flame Excitation Sources for Analytical Spectroscopy", vol. 40, No. 1, 1986, pp. XIX–XXVIII.
Snyder & Kirkland Introduction to Modern Liquid Chromatography, pp. 90–114, 1979 edition.
Welz, Atomabsorptionsspektrometrie, pp. 38–43, 270–271, 1983 edition.
Doherty & Hieftji, "Jet—Impact Nebulization for Sample Introduction in Inductivity Coupled Plasma Spectrometry", 1369 Applied Spectroscopy 38, pp. 405–412, (May/Jun. 1984).

Primary Examiner—Vincent P. McGraw
Attorney, Agent, or Firm—Lee & Smith

[57] ABSTRACT

For nebulizing sample liquid for spectroscopical purposes a liquid to be nebulized is pressurized to a minimum pressure of 30 bar through a high-pressure pump formed as a separate unit, and is nebulized through a nozzle having a smallest flow aperture of less than $5 \cdot 10^{-9}$ m². The high-pressure pump and the nozzle are interconnected through conduits. In one embodiment the pump takes in pure solvent. The sample is taken in on the high-pressure side through a loop, which is arranged to be connected between pump and nozzle.

19 Claims, 5 Drawing Sheets

DEVICE FOR NEBULIZING SAMPLE LIQUID FOR SPECTROSCOPICAL PURPOSES

This application is a continuation of Ser. No. 872,885, filed 6/11/86 and now abandoned.

The invention relates to a device for nebulizing sample liquid for spectroscopical purposes, in which a liquid to be nebulized is pumped under high pressure through a nozzle and nebulized by the nozzle.

The nebulized sample liquid can be sprayed into the mixer chamber of a burner for atomic absorption spectroscopy. A device of this type can, however, also be used to spray sample liquid into the plasma of a plasma burner for plasma emission spectroscopy.

For these purposes efforts are made to provide an aerosol distributed as finely as possible, that is an aerosol, in which the droplets formed are mainly very small. Bigger droplets are not or just partially vaporized, such that the sample substance gets lost for the measurement. In addition, the noise level increases due to dispersion, reflection and refraction of the radiation by the droplets.

Usually pneumatic nebulizers are used for nebulizing the sample liquid. Such pneumatic nebulizers comprise a nozzle, out of which a pressurized gas flow emerges. A tube is located coaxial in this nozzle, sample liquid being supplied through this tube. When the sample liquid enters the pressurized gas flow the sample liquid is torn to droplets due to the different velocities of the sample liquid flow and the pressurized gas flow. In such nebulizer, only a relatively small percentage of the sample liquid is nebulized to sufficiently small droplets. In order to keep bigger droplets away from the flame or the like, the sample liquid is, first of all, nebulized in a nebulizing chamber or mixer chamber. There the bigger droplets precipitate, whereas only the small droplets are entrained to the flame or the plasma.

In conventional pneumatic nebulizers the gas pressure is 2 to 6 bar. Higher gas pressures and thus higher flow rates of the gas flow supply too much gas to the flame or the plasma. It is true that this leads to a finer nebulization. However, the aerosol is diluted very much with air or rare gas. This would disturb the function of the flame or the plasma, respectively. In addition, the sensitivity is reduced due to the dilution of the aerosol.

From German Patent No. 1,950,989 a device for nebulizing sample liquid for spectroscopical purposes is known, which operates with a conventional pneumatic nebulizer. Therein a compressor is provided, which is connected to the nebulizer through a conduit. The compressor provides compressed air, the pressure of which is controlled through a pressure controller. This compressed air emerges at high velocity as an annular flow through a nebulizing nozzle. Due to the vacuum caused thereby, sample liquid is drawn in from a reservoir. The sample liquid is nebulized by the high flow rates of the air surrounding the sample liquid thus drawn in.

Furthermore there is known from the Journal "Industrie-Lackierbetrieb", 44th year (1976) No 6 pages 222-229 to nebulize lacquer with a spray gun, by pumping the lacquer through a nozzle by means of a high-pressure pump.

From German Offenlegungsschrift No. 30 10 350 a laminar burner for spectroscopical purposes is known, in which a liquid sample is drawn in and nebulized in a mixer chamber, intermixed with oxidizing agent and fuel gas and supplied to a burner head as aerosol. In this laminar burner a mechanical nebulizer is provided for nebulizing the sample. In this nebulizer the sample liquid is taken in by a pump, pressurized and nebulized through a valve nozzle. The nebulizer has a cylinder having a through-bore, in which a sample intake conduit ends laterally. A plunger is guided in the through-bore. This plunger extends out of the through-bore on one side. A valve nozzle is located on the other side of the through-bore. The valve nozzle consists of a valve cone, which engages the opening of the through-bore under the action of a biassed spring. A cap provided with a central nozzle opening and extending over the valve cone is screwed on the cylinder. By means of a driving device the plunger is driven to make rapid reciprocating movement.

In another embodiment of German Offenlegungsschrift No. 30 10 350 the nebulizer comprises a cylinder having a stepped through-bore which has a relatively wide portion at one end of the cylinder and a portion of smaller diameter at the other end, a shoulder being formed between the two portions. A sample intake conduit ends in the portion of smaller diameter at a short distance from the shoulder. A plunger is guided in this portion of the through-bore and extends out of the through-bore on one side. A narrow outlet nozzle closes the relatively wide portion of the through-bore. A valve body preloaded in closing direction engages the shoulder.

Also here, the plunger can be caused to make rapid reciprocating movements by means of a driving device.

The latter construction operates as follows:

During the return stroke of the plunger, sample liquid is taken in through the sample intake conduit. During this process, the valve formed by the valve body and the shoulder is closed. Therefore a high pressure can be maintained in the relatively wide portion of the through-bore, even during the intake stroke of the plunger. This pressure is gradually equalized through the narrow outlet nozzle. During the forward stroke of the plunger the opening of the sample intake conduit is covered by the plunger. The sample volume enclosed between this opening and the valve body is compressed heavily by the further stroke of the plunger until the valve body lifts off.

Thus high pressures are attained.

Such a device offers the advantage that no additional gas flow is necessary for nebulizing the sample liquid.

In the prior art nebulizer, pump and nozzle form an integrated component. Thus, the pump has to be mounted together with the nozzle and the drive for the pump directly on the burner. This results in design problems. Furthermore, in the prior art nebulizer pulsations occur in the spayed-in sample liquid vapour. Such pulsations are hard to control and, as explained there, are to be smoothed by the mixer chamber. Pulsations of the flow rate result, however, also in pulsations of the size of the droplets.

It is the object of the invention to provide a device for nebulizing liquid sample for spectroscopical purposes, which device permits well-defined nebulization of the sample liquid with a high yield of very small droplets, and its application with burners, plasma burners or other excitation and atomizing devices in spectroscopy without design problems.

According to the invention this object is achieved in that (a) the pump is a high-pressure pump formed as a separate unit and adapted to provide a minimum pressure of 30 bar, and (b) the nozzle connected to the pump through conducting means has a smallest flow aperture of less than $5 \cdot 10^{-9}$ m$^2$.

Due to the use of a separate high-pressure pump, only the nozzle has to be mounted on the burner, plasma burner or the like. This avoids design problems occurring with the arrangement according to German Offenlegungsschrift No. 30 10 350. High-pressure pumps are commercially available, for example, as high-pressure pumps for high-pressure liquid chromatography (HPLC). They provide a constant, not pulsating pressure. Thereby also the size of the droplets depending on this pressure remains constant. The high pressure and the small nozzle opening ensure high exit velocity and thus fine nebulization of the sample liquid with a high percentage of very small droplets. The nozzle, however, is so small that, at the high pressure, also small sample quantities can be sprayed in throughout a sufficiently long measuring time.

Modifications of the invention are subject matter of the subclaims.

Some embodiments of the invention will now be described in greater detail with reference to the accompanying drawings:

FIG. 1 is a schematic illustration of a burner with a device for nebulizing sample liquid.

FIG. 2 shows the nozzle in the embodiment of FIG. 1.

FIG. 3 shows a modification of the embodiment of FIG. 1, with which a pulsed nebulization is possible.

FIG. 4 shows a burner with a device for nebulizing sample liquid, with which a well-defined quantity of sample liquid is nebulized in a short time at very high pressure.

FIG. 5 shows an arrangement for feeding nebulized sample liquid immediately into a plasma burner.

FIG. 6 shows an arrangement for feeding nebulized sample liquid immediately into a tube furnace which is heated to high temperature either like a graphite tube atomizer by passing electrical current therethrough or by a flame, a measuring light beam passing through the tube furnace along its axis.

FIG. 7 shows a section through a preferably used hollow cone nozzle.

FIG. 8 shows an arrangement for feeding nebulized sample liquid immediately into a turbulent burner.

In the embodiment of FIG. 1, numeral 10 designates a burner having a mixer chamber 12 and a burner head 14. A flame 16 burns on the burner head 14. A fuel gas, for example acetylene, is supplied to the mixer chamber 12 through a port 18, and air is supplied through a port 20. Air and fuel gas intermingle in the mixer chamber 12. A liquid vapour is sprayed into the mixer chamber 12 by a nozzle 22. Liquid precipitated from the liquid vapour in the mixer chamber 12 can be drained off through an outlet 23. The gases supplied through the ports 18 and 20 transport the liquid nebule provided by the nozzle 22 into the flame.

The device for nebulizing sample liquid comprises a high-pressure pump 24 and the nozzle 22. High-pressure pump 24 and nozzle 22 are interconnected through conducting means 26. The high-pressure pump 24 is a double-piston pump as commercially available for high-pressure liquid chromatography. A pump usable therefor is sold by the company LDC/Milton Ray at Riviera Beach, Fla. 33004 U.S.A., under the trade mark "constaMetric III". Such a high-pressure pump provides a pulse-free stabilized pressure with flow rates from 0.1 to 99.9 ml/min with a flow rate stability of ±0.3%/h and a maximum pressure of 6000 psi.

The pump 24 sucks liquid from a container 30 through a filter 27 connected upstream of the inlet 28 of the pump 24. An outlet 32 of the high-pressure pump 24 is connected to the nozzle 22 through the conducting means 26. The conducting means 26 comprise a high-pressure capillary 34. In the embodiment illustrated in FIG. 1, the conducting means 26 comprise, between the outlet 32 of the high-pressure pump 24 and the nozzle 22, a loop adapted to be filled with sample liquid, and change-over valve means which are arranged to selectively connect the loop into the flow path between high-pressure pump 24 and nozzle. These change-over valve means including the loop are illustrated in FIG. 1 by the block 36. These can be components known also from high-pressure liquid chromatography. Examples for such valves are described in the company brochure "Das Chrompack Chromatographie-Handbuch Generalkatalog" of Messrs. Chrompack, 4330 AA Middelburg, Netherlands, pages 126–140.

The nozzle 22 is illustrated at an enlarged scale in FIG. 2.

Through the high-pressure capillary 34 the liquid gets into the interior 38 of the nozzle 22 and from there to a narrow outlet opening 40. The connection between high-pressure capillary 34 and nozzle 22 is made by an conventional high-pressure port 41, as also known, for example, from high-pressure liquid chromatography.

The high-pressure pump operates with a pressure of more than 30 bar. The nozzle has a diameter smaller than 40 μm, i.e. the smallest flow aperture of the nozzle is less than $1.3 \cdot 10^{-9}\ m^2$.

The arrangement described can operate in two different modes:

The sample can be placed into the container 30. Then the valve means 36 are switched such that a continuous connection is established between the outlet 32 of the high-pressure pump 24 and the nozzle 22. Then sample liquid is taken in by the high-pressure pump 24 from the container 30 through the filter 27 and the inlet 28 and supplied continuously at high pressure of at least 30 bar through the outlet 32 and the high-pressure capillary 34 to the nozzle 22. This leads to fine nebulization of the sample. The mist of sample liquid thus generated is taken along into the burner head 14 by the gases supplied through the ports 18 and 20. The fine droplets are quickly vaporized in the flame 16 and atomized. Thus, a "cloud of atoms" is formed in the flame. A measuring light beam composed of the resonance lines of an element looked for is absorbed depending on the quantity of the element locked for in the sample. Thus, in a known way, a measuring value for the percentage of the element looked for in the sample liquid can be obtained.

When sucking sample liquid by means of the high-pressure pump 24 from the container 30 a relatively large quantity of sample liquid is used up because, for example, the pump cylinder has to be filled with sample liquid. Often there is not that much sample available. A further problem is that sample liquids often are aggressive, such that there is risk of damage of the high-pressure pump 24. Finally there is the risk of cross-contamination, when different samples are measured successively.

These problems are avoided by using a loop with change-over valve means 36. With this made, the container 30 contains pure solvent. This solvent is placed under high pressure by the high-pressure pump 24. The sample is filled into the loop which is adapted to be connected into the flow connection between high-pressure pump 24 and nozzle 22 by the change-over valve means 36 upon a change-over command. Thereby the sample liquid is exposed indirectly to the high output pressure of the high-pressure pump 24, namely through the solvent delivered, and is pressed through the nozzle 22 by the solvent. This arrangement has the advantage that the high-pressure pump 24 comes into contact only with pure solvent. Thereby the risk of cross-contamination of samples and the risk of corrosion of the high-pressure pump 24 by aggressive samples is avoided. Only the device 36, the high-pressure capillary 34 and the nozzle 22 have to be corrosion-proof. After the sample has passed through, the loop and the high-pressure capillary 34 are rinsed by the following pure solvent, such that the risk of cross-contamination is avoided. With the latter mode of operation, it can be advantageous to arrange a filter between the change-over valve means 36 and the nozzle 22. Such a filter is shown in FIG. 1 by the dotted line and designated by 31'.

Filters usable for this are illustrated on page 118 of the above mentioned catalogue for low pressure and high pressure.

Figure 3:
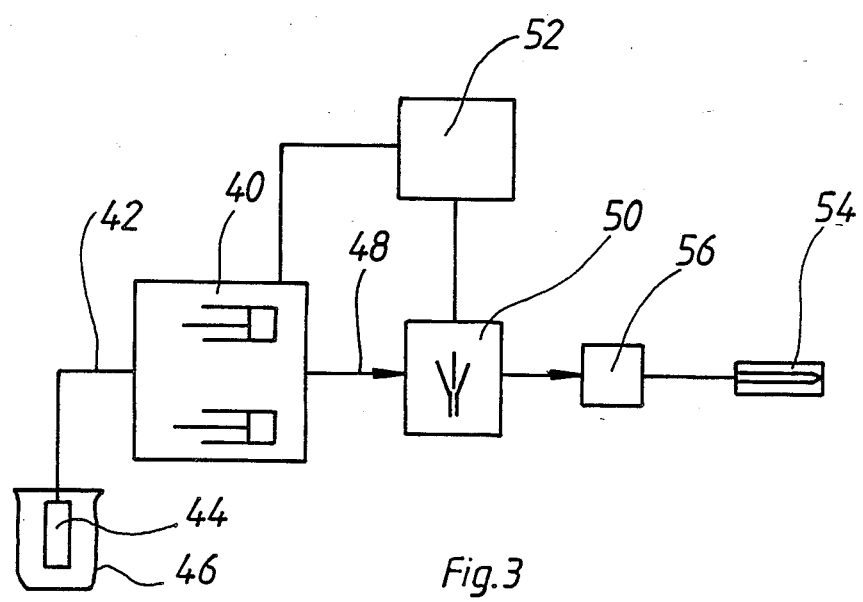

In the embodiment of FIG. 3 a pulsed nebulizer is used. A high-pressure pump 40, which can be of a similar type as the pump 24 shows in FIG. 1 and which is adapted to provide a continuous liquid flow at constant pressure, sucks liquid through an inlet 42 and a filter 44 from a container 46. An outlet 48 of the high-pressure pump 40 is connected to a controlled valve 50. This controlled valve is arranged to be actuated by an electronic control device 52 at a large rate of cycles (for example, 10 to 100/s), such that the liquid flow is pulsed at this frequency. Preferably the valve is a needle valve. The liquid flow thus provided is supplied to the nozzle 54.

This arrangement offers the advantage that, at a predetermined average flow rate of, for example, 1 ml/min., it can be operated at higher pressures with the same diameter of the nozzle. An increase of the pressure with the same diameter of the nozzle in order to achieve a higher exit speed of the sample liquid at the nozzle, and thus finer nebulization, would, at continuous pressure, result in a corresponding increase of the flow rate and thus a faster consumption of the sample liquid. Due to the pulsation of the liquid flow the pressure can be increased without the average flow rate exceeding a predetermined value. When, however, a high-pressure pump 40 of the present type is used, the nozzle 54 is exposed to the entire pressure after the valve 50 has been opened. In this respect the arrangement of FIG. 3 is different from an arrangement as disclosed, for example, in German Offenlegungsschrift No. 30 10 350, in which the pump provides a pulsating pressure and in which thus in the range of lower pressures larger droplets are formed in the mist of sample liquid.

The arrangement of FIG. 3 like the arrangement of FIG. 1 can be used in different modes. Sample liquid can be sucked directly from the container 46. But it is also possible to bring the sample into a loop which is connected into the flow path between valve 50 and nozzle 54 by means of change-over valve means. The loop and the change-over valve means are illustrated by a block 56 in FIG. 3.

The order of the valve 50 and the loop and change-over valve means 56 can also be reversed.

The high pressure pump 40 can be connected to the electronic control unit 52 for synchronization.

Figure 4:
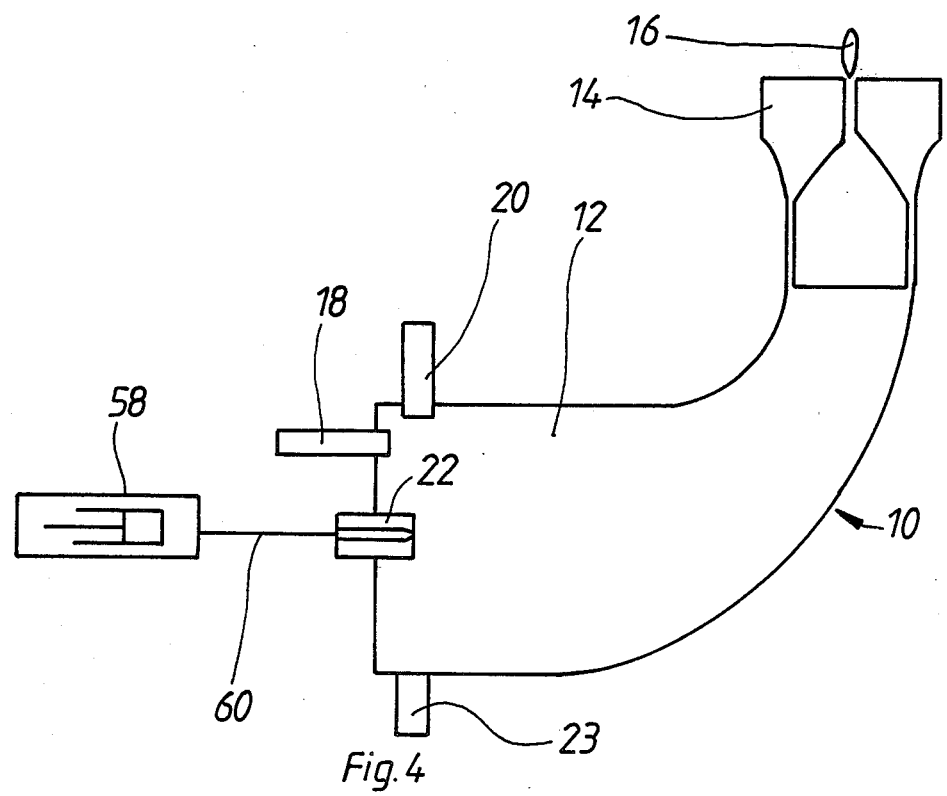

In the embodiment of FIG. 4 the high-pressure pump is a high-pressure pulse generator 58, which presses a predetermined volume in the range of microliters (for example 50 μl) of sample liquid through the nozzle 22 in a short time interval. The high-pressure pulse generator 58 is connected directly to the nozzle 22 through conducting means 60. The nozzle 22 is located in the wall of a mixer chamber 12 of a burner 10, which is constructed in the same way as the burner 10 in FIG. 1. Corresponding elements are designated in FIG. 4 by the same numerals as in FIG. 1.

A high-pressure pulse generator adapted to be used for the present purposes is described in the paper by K.Melcher "Ein Reibungsmodell zur Berechnung von instationären Strömungen in Rohrleitungen an Brennkraftmaschinen", Bosch Tech.Berichte, Volume 4 (1979) Issue 7, pages 273–290.

Figure 5:
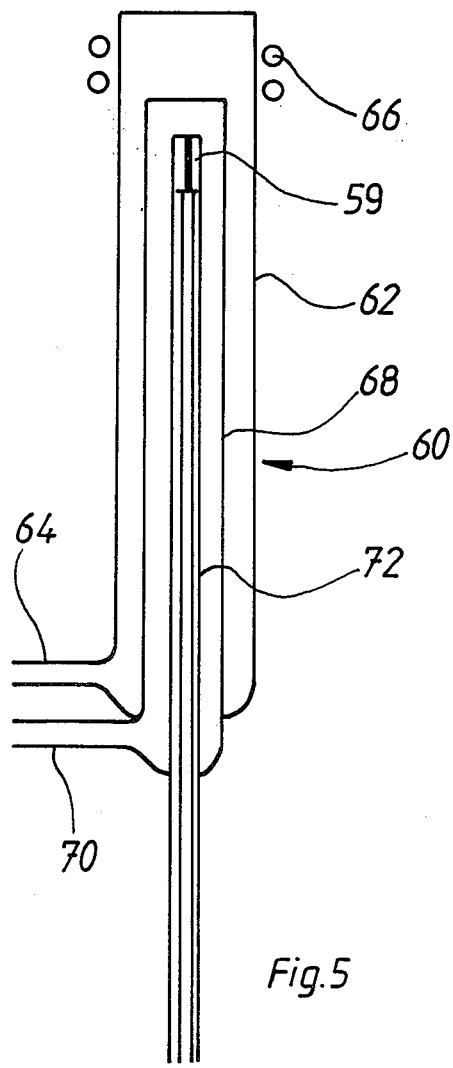

In the embodiment illustrated in FIG. 5, the aerosol is sprayed by a nozzle 59 directly into the plasma of a plasma burner 60. The nozzle 59 is arranged centrally in the plasma burner 60. The plasma burner 60 has an external tube 62 open at one end. A rare gas to be ionized in the form of argon is supplied to this tube 62 through a port 64. The external tube 62 is surrounded by an exciting coil 66 at its open end. Furthermore, the plasma burner 60 has an internal tube 68 coaxial to the external tube 62. This internal tube 68 ends below the exciting coil 66. Rare gas, likewise in the form of argon, is passed as coolant through the internal tube 68 and through a port 70. A capillary 72 extends coaxially inside the internal tube 68. This capillary 72 is connected to a high-pressure pump (not shown) in the manner illustrated in FIGS. 1, 3 or 4, and carries the nozzle 59 at its end.

Figure 6:
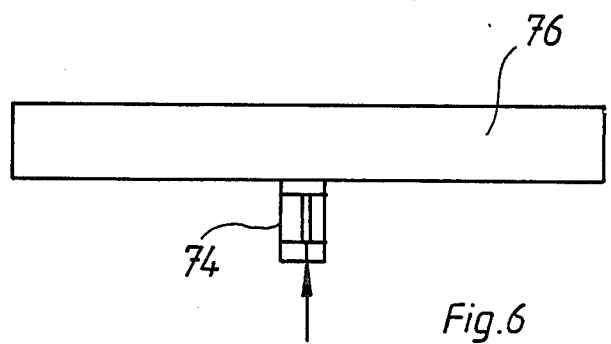

In the embodiment of FIG. 6, a nozzle 74 is attached directly to a tube furnace 76. The tube furnace 76 can be a quartz tube located in the flame of a burner for atomic absorption spectroscopy. It can also be a tube which is heated in the way of a graphite tube atomizer by electrical resistance heating. The interior of the tube forms a well-defined absorption volume in atomic absorption spectrometry. The sample liquid under high pressure can be supplied to the nozzle 74 in anyone of the ways illustrated in FIGS. 1, 3 and 4.

Figure 7:
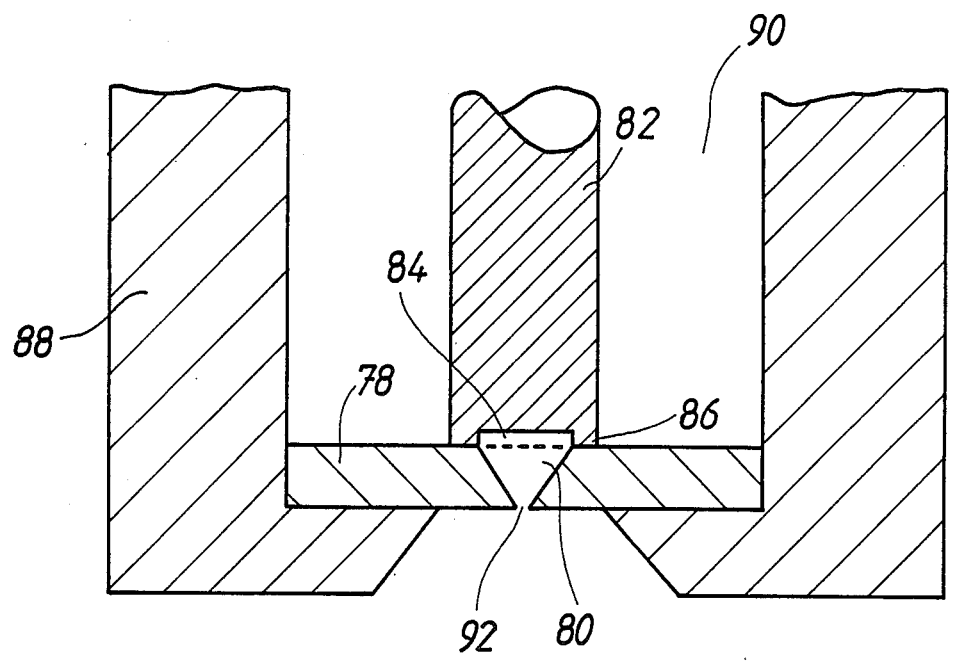

FIG. 7 shows an advantageous construction of a nozzle used in the described device. The nozzle is formed as a so called "hollow cone nozzle". The advantage of such a hollow cone nozzle is that the narrowest point for imparting highspeed to the liquid to be nebulized is located in the interior of the nozzle. Thereby the real nebulization opening, for example, the outlet opening toward the mixer chamber 12 (FIG. 1), can be relatively large, for example, have a diameter of 100 μm.

A hollow cone 80 is formed in a small plate 78. The hollow cone 80 is closed towards the top by a cylinder 82, which has a recess 84 in its end face. At one location of the cylinder 82, a tangential inlet opening 86 of minimized diameter is notched. In order to reduce the outlet resistance, the notch has a conical form, that means it is narrow at its inlet into the hollow cone 80, for example, with a diameter of 20 μm, while it is large on the side of the fluid inlet, for example, with a diameter of 100 μm.

The plate 78 is held by a housing 88. The cylinder 82 provides for the necessary contact pressure of the plate 78 against the housing 88. The fluid under high pressure from the pump 24 is in the space 90 between cylinder 82 and housing 88, reaches the hollow cone 80 through the inlet opening 86 and is nebulized at an outlet opening 92.

With a continuous liquid pressure at the nozzle, a pressure higher than 30 bar and a nozzle opening having a smallest flow aperture of $1,3 \cdot 10^{-9}$ m$^2$ are used. If the liquid is pulse-pressurized, a pressure of more than 150 bar and a smallest flow aperture of the nozzle of $5 \cdot 10^{-9}$ m$^2$ are used.

Figure 8:
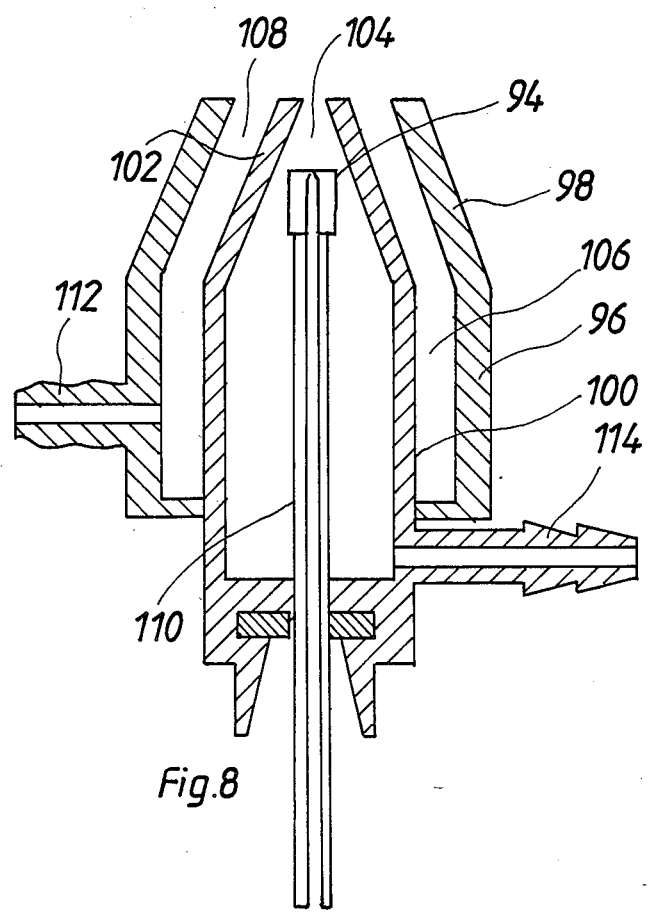

FIG. 8 shows an arrangement in which the nozzle 94 exposed to sample liquid under high pressure is arranged centrally in a so called "turbulent burner". Such a turbulent burner comprises an external jacket 96 having a conical upper end 98. An internal jacket 100 also having a conical upper end 102 is arranged coaxially to the external jacket 96. The internal jacket 100 forms, at its top, a narrow outlet opening 104. An annulus 106 is formed between the external jacket 96 and the internal jacket 100. The annulus 106 ends in an annular slot 108 between the conical ends 98 and 102. A capillary 110 is located coaxially in the internal jacket 100 and carries the nozzle 94 at its end below the outlet opening. The annulus 106 can be connected to a fuel gas source through a port 112. The interior of the internal jacket 100 can be connected to a source of oxidizing agent through a port 114.

Such turbulent burners usually suffer from the disadvantage that a large number of big droplets reach the flame. Thereby vaporization is only partial and the spectral background is increased considerably. If, however, instead of the conventional intake capillary a pressure-proof capillary 110 carrying the nozzle 94 at its upper end is inserted into such a turbulent burner, the substantial disadvantages of the turbulent burner are overcome. Its advantages will become effective, for example, that the entire sample reaches the flame.

I claim:

1. A device for nebulizing sample liquid for spectroscopical purposes, comprising:
   (a) a nozzle means for converting high pressure of a fluid supplied to an inlet orifice thereof to high speed of said fluid emerging from an outlet orifice, and
   (b) high pressure pump means for supplying fluid under high pressure to said inlet orifice to nebulize said fluid by its own high outlet speed at the outlet of said nozzle,
   wherein
   (c) said high pressure pump means comprise a separate high pressure pump unit means for providing an output pressure of at least 30 bar,
   (d) said high pressure pump unit is arranged remote from the nozzle and connected to said nozzle through conducting means for supplying said high pressure from the high pressure pump means to said inlet orifice; and
   (e) said outlet orifice has a flow aperture of less than $5.10^{-9}$m$^2$.

2. A device as claimed in claim 1, wherein said nozzle has a relatively large flow aperture inlet orifice and a relatively small flow aperture outlet orifice and tapering inner wall therebetween.

3. Device as set forth in claim 1, characterized in that
   (a) the high-pressure pump (24) is a continuously feeding pump having an inlet (28) and an outlet (32),
   (b) the inlet (28) of the high-pressure pump (24) is connected to a solvent reservoir (27),
   (c) the conducting means (26) between the outlet (32) of the high-pressure pump (24) and the nozzle (22) comprise a loop adapted to be filled with sample liquid, and change-over valve means (36), through which the loop is adapted to be selectively connected into the flow path between high-pressure pump (24) and nozzle (22).

4. Device as set forth in claim 2 characterized in that a filter (27) is connected upstream of the inlet (28) of the high-pressure pump (24).

5. Device as set forth in claim 2 characterized in that a filter (31) arranged on the high pressure side of the high-pressure pump is connected upstream of the nozzle (22).

6. Device as set forth in claim 2, characterized in that the high-pressure pump (24) is a multiplunger pump.

7. Device as set forth in claim 1, characterized in that
   (a) the high-pressure pump (58) is a high-pressure pulse generator, through which a predetermined volume of sample liquid is pressed through the nozzle during a short time interval, and
   (b) the high-pressure pulse generator is designed for generating a pressure of at least 150 bar for a short time.

8. Device as set forth in claim 2, characterized in that controlled valve means (50) are provided between the high-pressure pump (40) and the nozzle (54), which valve means (50) are arranged to cause a pulsed nebulization.

9. Device ads set forth in claim 1, characterized in that the nozzle (59) is arranged centrally in a plasma burner (60).

10. Device as set forth in claim 9, characterized in that
    (a) the plasma burner (60) has an external tube (62) open at one end, a gas to be ionized being supplied to said tube (62), said tube (62) being surrounded by an exciting coil (66) at its open end,
    (b) the plasma burner (60) furthermore comprises an internal tube (68) coaxial to the external tube (62), said internal tube (68) ending below the exciting coil (66), a further gas being passed through said internal tube, and
    (c) a capillary (72) extends coaxially inside the internal tube (68) and is connected to the high-pressure pump and carries the nozzle (59) at its end.

11. Device as set forth in claim 1, characterized in that the aerosol provided by the nozzle (74) is passed into a tube furnace (76).

12. Device as set forth in claim 1, characterized in that the nozzle is a hollow cone nozzle (FIG. 7).

13. Device as set forth in claim 1, characterized in that the nozzle is arranged centrally in a turbulent burner.

14. Device as set forth in claim 13, characterized in that
    (a) the turbulent burner has an internal jacket (100) and an external jacket (96), oxidizing agent and fuel gas are passed coaxially through internal and external jacket and the gases are intermingled outside the turbulent burner, and
    (b) a capillary (110) extends in the interior of the internal jacket and carries the nozzle (94) at its end.

15. Device as set forth in claim 3, characterized in that a filter (27) is connected upstream of the inlet (28) of the high-pressure pump (24).

16. Device as set forth in claim 3, characterized in that a filter (27) arranged on the high pressure side of the high-pressure pump is connected upstream of the nozzle (22).

17. Device as set forth in claim 3, characterized in that the high-pressure pump (24) is a multiplunger pump.

18. Device as set forth in claim 2, characterized in that the nozzle is arranged centrally in a turbulent burner.

19. Device as set forth in claim 3, characterized in that the nozzle is arranged centrally in a turbulent burner.

* * * * *